(12) United States Patent
Margheritis et al.

(10) Patent No.: US 8,016,165 B2
(45) Date of Patent: Sep. 13, 2011

(54) FLUID PRODUCT DISPENSING DEVICE

(75) Inventors: Antonio Margheritis, Cittiglio (IT); Samuel Pruvot, Saint Etienne du Vauvray (FR); Ludovic Petit, Vitot (FR); Serge Herry, Quatremare (FR); Christophe Fagot, Mezy (FR)

(73) Assignee: Valois SAS, Le Neubourg (FR)

( * ) Notice: Subject to any disclaimer, the term of this patent is extended or adjusted under 35 U.S.C. 154(b) by 874 days.

(21) Appl. No.: 11/629,468

(22) PCT Filed: Jun. 16, 2005

(86) PCT No.: PCT/FR2005/050454
§ 371 (c)(1),
(2), (4) Date: Dec. 14, 2006

(87) PCT Pub. No.: WO2006/003343
PCT Pub. Date: Jan. 12, 2006

(65) Prior Publication Data
US 2008/0029544 A1    Feb. 7, 2008

(30) Foreign Application Priority Data
Jun. 16, 2004 (FR) .................... 04 06526

(51) Int. Cl.
*B65D 88/54*    (2006.01)
(52) U.S. Cl. ............ 222/321.6; 222/321.7; 222/340; 222/380; 239/333

(58) Field of Classification Search .......... 222/321.6, 222/380, 321.7, 385, 321.9, 321.1, 340, 321.2, 222/383.1, 321.8; 239/333
See application file for complete search history.

(56) References Cited

U.S. PATENT DOCUMENTS

| | | | | |
|---|---|---|---|---|
| 4,402,432 A * | 9/1983 | Corsette | ............ | 222/321.2 |
| 4,458,832 A * | 7/1984 | Corsette | ............ | 222/153.13 |
| 4,494,680 A * | 1/1985 | Corsette | ............ | 222/321.3 |
| 4,503,997 A * | 3/1985 | Corsette | ............ | 222/321.9 |
| 4,591,077 A * | 5/1986 | Corsette | ............ | 222/321.3 |
| 4,640,443 A * | 2/1987 | Corsette | ............ | 222/321.3 |
| 5,503,306 A | 4/1996 | Knickerbocker | | |
| 5,720,419 A * | 2/1998 | Li | ............ | 222/321.2 |
| 7,182,226 B2 * | 2/2007 | Mbonyumuhire | ............ | 222/321.7 |
| 2002/0100772 A1 * | 8/2002 | Bonningue | ............ | 222/321.2 |

FOREIGN PATENT DOCUMENTS

| | | | |
|---|---|---|---|
| EP | 1295646 A1 * | 3/2003 | |
| ES | 375 103 A1 | 3/1972 | |
| FR | 2 475 641 A | 8/1981 | |
| FR | 2 547 364 A | 12/1984 | |

* cited by examiner

Primary Examiner — Frederick C. Nicolas
(74) Attorney, Agent, or Firm — Sughrue Mion, PLLC

(57) ABSTRACT

A fluid dispenser device including: a reservoir (10); a dispenser head (20) incorporating a dispenser orifice (21); a metering chamber (30); and a piston (40) that is slidable in the metering chamber (30) between a rest position and a dispensing position. The piston (40) is mounted in stationary manner on the reservoir (10) and made integrally with the reservoir (10) and/or with a fastener mechanism (100) adapted to be fastened on the reservoir (10).

31 Claims, 8 Drawing Sheets

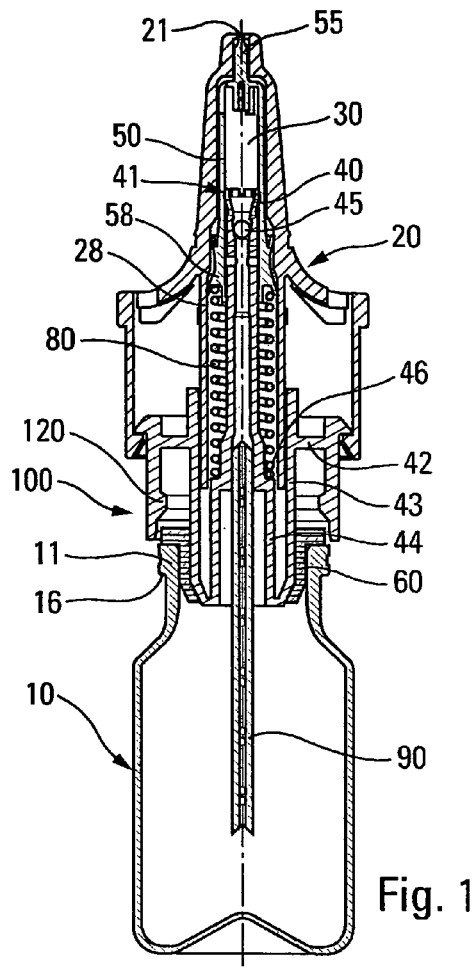
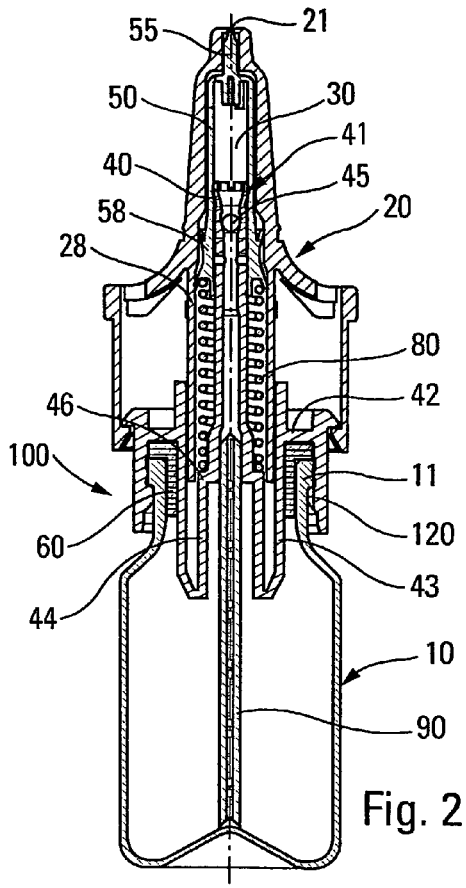
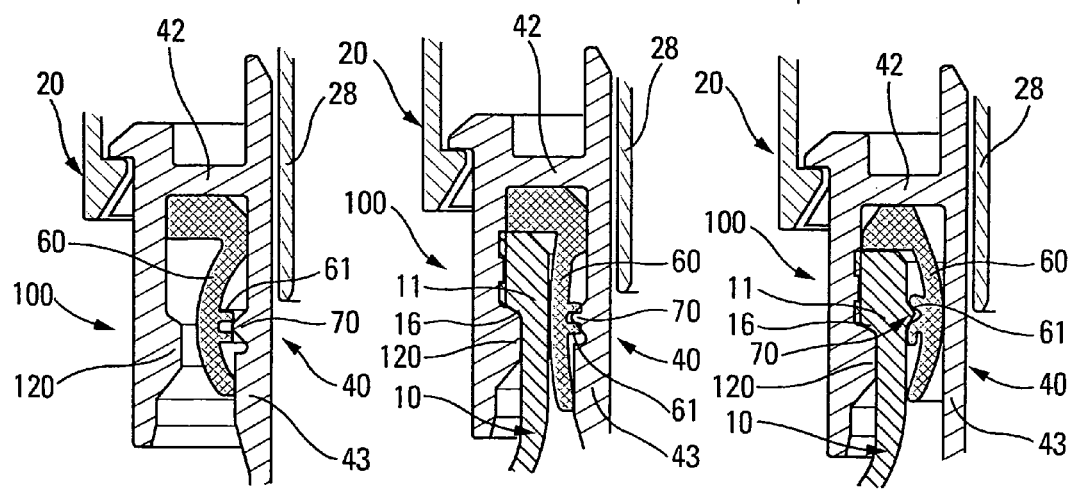
Fig. 1  Fig. 2
Fig. 3a  Fig. 3b  Fig. 4

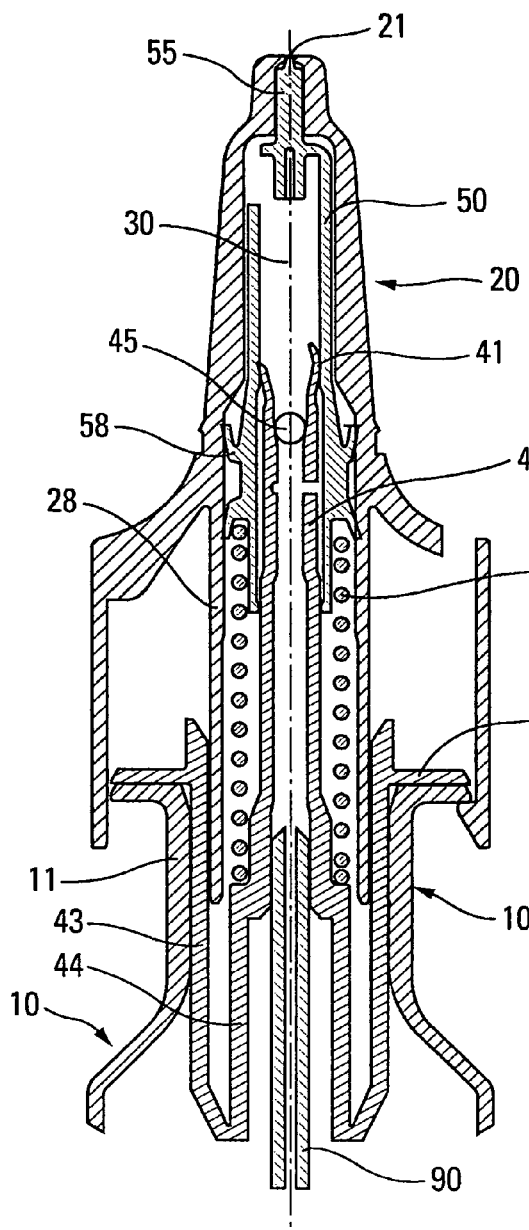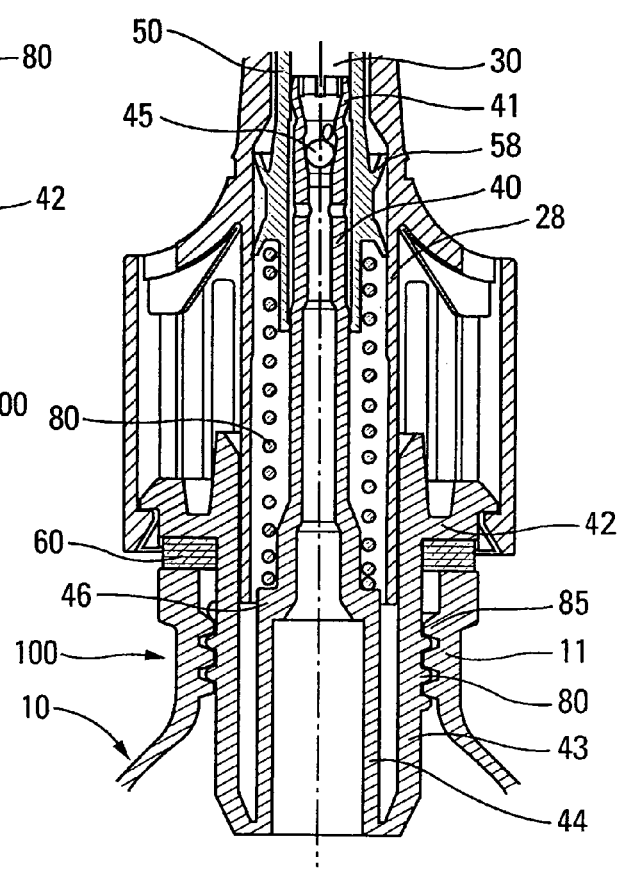
Fig. 5
Fig. 6

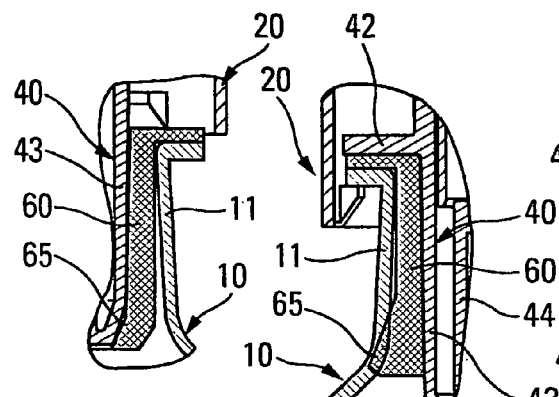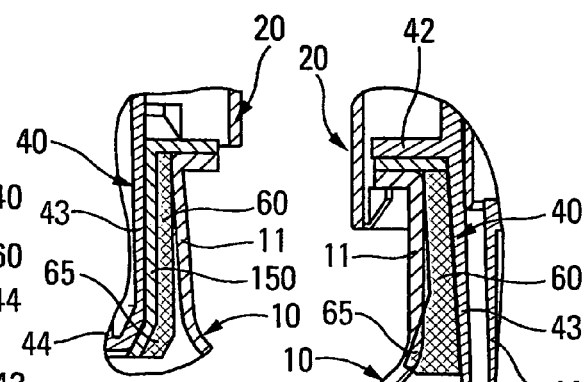
Fig. 16  Fig. 17  Fig. 18  Fig. 19
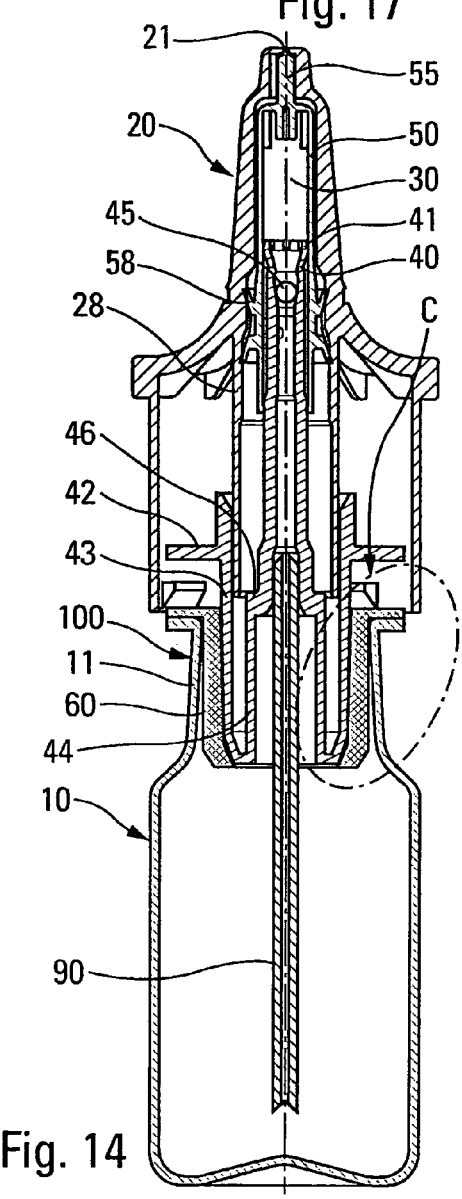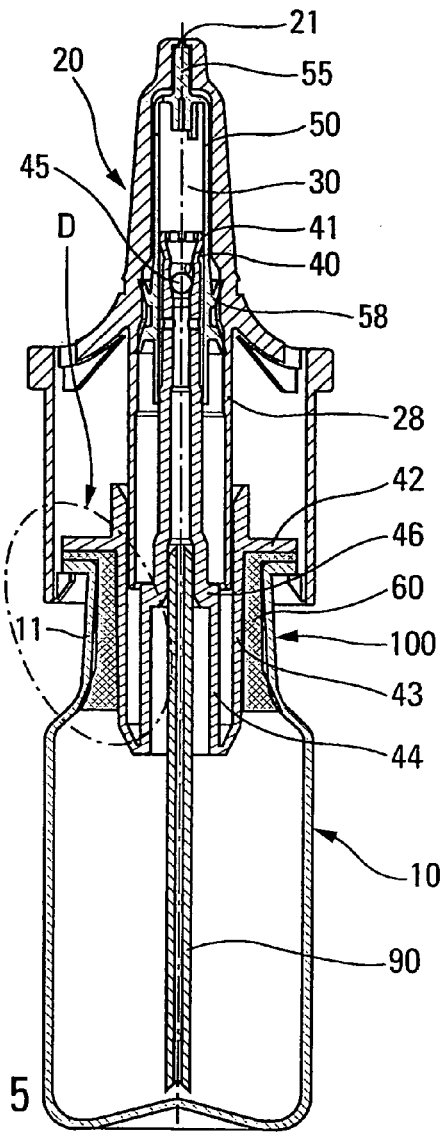
Fig. 14  Fig. 15

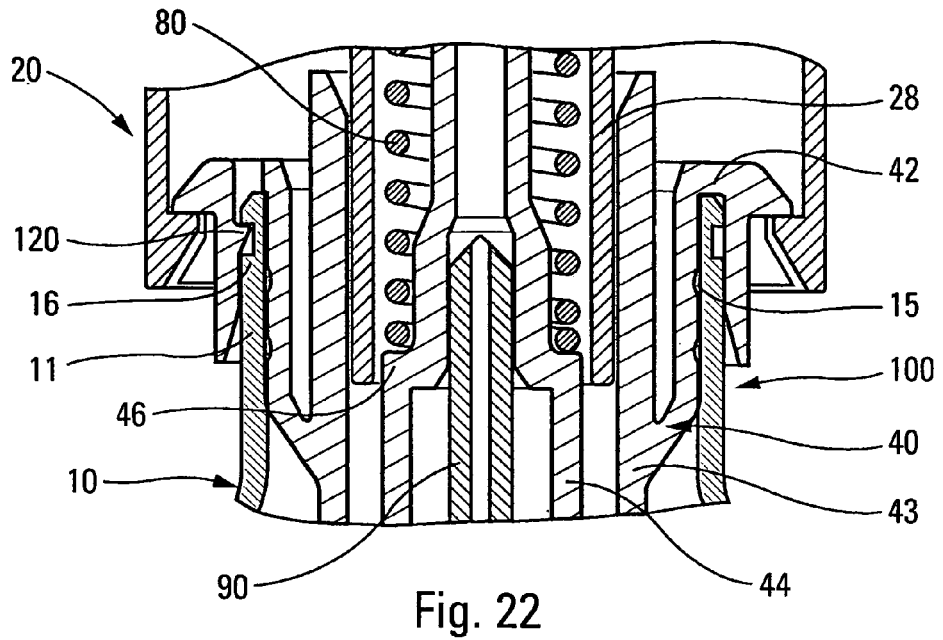
Fig. 22
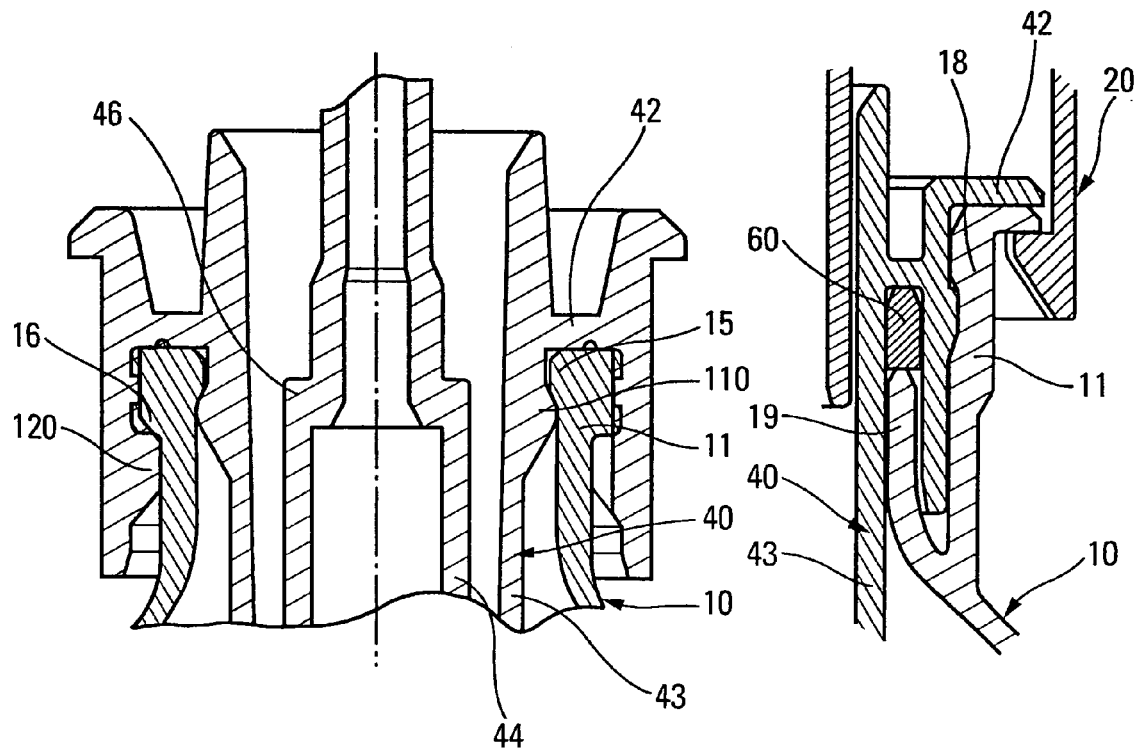
Fig. 23
Fig. 24

FLUID PRODUCT DISPENSING DEVICE

The present invention relates to a fluid dispenser device.

Fluid dispenser devices generally comprise: a reservoir containing the fluid (liquid, paste, or powder) to be dispensed; and a dispenser member mounted on said reservoir, such as a pump or a valve, for selectively dispensing the content of said reservoir. A dispenser head is assembled on the dispenser member so as to actuate said dispenser member, in order to dispense one dose of fluid manually at each actuation. When the dispenser member is a pump, the pump generally includes a pump body defining a metering pump chamber in which a piston slides between a rest position and a dispensing position. The piston is displaced from its rest position towards its dispensing position by pressure exerted by the user on the dispenser head. The metering chamber may include an inlet valve and an outlet valve, and the device may include a closure member in its dispenser orifice that is generally provided in the dispenser head. In conventional manner, the pump body is generally fastened on the reservoir in any known manner, e.g. by means of a fastener ring. The piston is thus slidably mounted inside said pump body, and it is displaced by said dispenser head. That construction presents a certain number of drawbacks. Thus, the slide surface of the piston in the pump body must be completely smooth and even, so as to avoid any malfunctioning of the pump, such as a loss of sealing or a blockage of the piston. This imposes very substantial precautions while the pump body is being assembled on the reservoir, so as to avoid the pump body being deformed during assembly. In particular, some assembly methods are very difficult to achieve when it is desired to fasten a pump body on a reservoir neck. This is particularly true when they involve snap-fastening inside the neck, since, if the neck is rigid, it is generally necessary to be able to deform the snap-fastenable portion, namely the pump body, thereby generating a risk of deforming the slide surface of the piston, leading to the above-mentioned drawbacks.

Another drawback of conventional pumps is that the metering chamber is generally disposed relatively far from the dispenser orifice, and it is thus necessary to provide both an outlet valve from the metering chamber so as to accurately define the metered dose, and a closure member in the dispenser orifice so as to avoid any risk of contaminating the fluid between two actuations. In addition, this generally implies using two springs, one for returning the piston towards its rest position, and the other for urging the closure member towards its closed position.

In addition, another drawback of existing pumps is associated with assembly that provides for fastening a pump (or some elements of the pump) on a reservoir by means of a fastener ring or the like. When the portion of pump to be fastened is the pump body, assembly of said pump body on the reservoir by means of a fastener ring does not present a major problem, but nevertheless requires two distinct assembly steps (pre-assembly of the pump body in the ring or on the reservoir, then fastening of the ring). When the pump element to be assembled on the reservoir is an internal part of the pump, assembly may turn out to be more difficult and may risk damaging the sealing portions of said element. This results in a pump that is generally complex to manufacture and to assemble, which can turn out to be detrimental with regard to the performance and the cost of the pump.

An object of the present invention is to provide a fluid dispenser device that does not have the above-mentioned drawbacks.

More particularly, an object of the present invention is to provide such a fluid dispenser device that eliminates any risk of spoiling the slide surface of the piston while the device is being assembled.

Another object of the present invention is to provide such a fluid dispenser device that comprises a minimum number of component parts. In particular, the invention eliminates one assembly part by making the piston integrally with the fastener means, or two assembly parts by making the piston integrally with the reservoir. In addition, the invention eliminates the need to have both an outlet valve for the metering chamber and a closure member for the dispenser orifice, and makes it possible to make a pump with a closure member that includes only one spring.

Another object of the present invention is to provide such a fluid dispenser device that is simple and inexpensive to manufacture and to assemble, that is safe and reliable in operation, and that avoids any risk of contaminating the fluid contained in said device.

The present invention thus provides a fluid dispenser device comprising: a reservoir; a dispenser head incorporating a dispenser orifice; a metering chamber; and a piston that is slidable in said metering chamber between a rest position and a dispensing position, said piston being mounted in stationary manner on said reservoir, said piston being made integrally with said reservoir and/or with fastener means that are adapted to be fastened on said reservoir.

Advantageously, said piston is fastened on the reservoir by fastener means, said fastener means being connected integrally with said piston.

Advantageously, said fastener means are snap-fastener, force-fit, or screw-fastener means.

In a first variant embodiment, said piston is fastened to the outside of a neck of said reservoir.

In a second variant embodiment, said piston is fastened to the inside of a neck of said reservoir.

In a third variant embodiment, said piston is fastened both to the outside and to the inside of a neck of said reservoir.

In a fourth variant embodiment, said piston is made integrally with said reservoir.

Advantageously, said piston slides in a pump body disposed in the dispenser head.

Advantageously, said pump body forms part of a closure member that is slidable in said dispenser head between a closed position and an open position of the dispenser orifice.

Advantageously, said closure member includes a second piston that is slidable in a cylinder of said dispenser head.

Advantageously, said piston includes an inlet valve of the pump chamber.

Advantageously, said piston is fastened on the reservoir with a gasket interposed between the piston and the reservoir.

Advantageously, said gasket is deformed while said piston is being fastened on said reservoir.

Advantageously, the piston includes fastener means co-operating with the outside of a neck of the reservoir, said gasket co-operating with the inside of said neck.

In a variant, the piston includes fastener means co-operating with the inside of a neck of the reservoir.

Advantageously, said fastener means include said gasket that is deformed between the piston and the inside of the neck of the reservoir, so as to fasten the piston in said neck by a leaktight force fit.

Advantageously, one amongst the inside surface of the neck of the reservoir and the corresponding outside surface of the piston includes a sealing profile co-operating with said gasket in the mounted state, preferably with a complementary sealing profile of said gasket.

Advantageously, said gasket includes a projection that, while the piston is being fitted by force, is itself deformed below the neck of the reservoir, inside said reservoir, so as to fasten the piston in permanent manner.

Advantageously, said piston includes snap-fastener means co-operating with the inside surface and/or the outside surface of a neck of said reservoir.

Advantageously, said snap-fastener means comprise a snap-fastener profile that is adapted to be snap-fastened in said neck or around said neck.

Advantageously, said neck includes a complementary snap-fastener profile co-operating with said snap-fastener profile of said piston.

Advantageously, the piston includes a screw thread co-operating with a corresponding thread provided on the inside or on the outside a neck of said reservoir.

Advantageously, at least one of said threads includes means for preventing unscrewing, such as a broken portion.

Advantageously, said piston includes first snap-fastener means co-operating with the inside of a neck of the reservoir, and second snap-fastener means co-operating with the outside of said neck.

Advantageously, the inside and/or the outside of said neck includes a complementary snap-fastener profile.

Advantageously, the top edge of a neck of the reservoir includes two axial branches each co-operating with said piston, preferably with a gasket being interposed therebetween.

Advantageously, said fastener means are formed directly on the piston.

Advantageously, a bushing is interposed between the piston and a neck of said reservoir.

Advantageously, said fastener means are formed on said bushing.

Advantageously, a gasket is interposed between said bushing and the neck of the reservoir.

Advantageously, said piston is force fitted directly inside a neck of said reservoir.

Other characteristics and advantages of the present invention appear more clearly from the following detailed description of several embodiments thereof, given by way of non-limiting example, and with reference to the accompanying drawings, and in which:

FIGS. 1 and 2 are diagrammatic section views of a fluid dispenser device constituting an advantageous embodiment of the present invention, respectively before and after assembly;

FIGS. 3a and 3b are detail views of a variant embodiment of the fastener means, respectively before and after assembly;

FIG. 4 is a view similar to the view in FIG. 3b, showing another variant embodiment of the fastener means, in the assembled position;

FIG. 5 is a diagrammatic and fragmentary section view of a fluid dispenser device constituting another advantageous embodiment of the invention;

FIG. 6 is a fragmentary section view of another variant embodiment of a fluid dispenser device of the invention;

FIGS. 14 and 15 are diagrammatic section views of a fluid dispenser device constituting still another embodiment of the present invention, respectively before and after assembly;

FIGS. 16 and 17 are diagrammatic section views of details C and D in FIGS. 14 and 15;

FIGS. 18 and 19 are views similar to the views in FIGS. 16 and 17, showing variant embodiments of the invention;

FIG. 22 is a diagrammatic section view of a detail E in FIG. 20;

FIG. 23 is a view similar to the view in FIG. 22, showing a variant embodiment of the present invention; and FIG. 24 is a fragmentary and diagrammatic section view of still another variant of the fastener means of the present invention.

Figure 7:
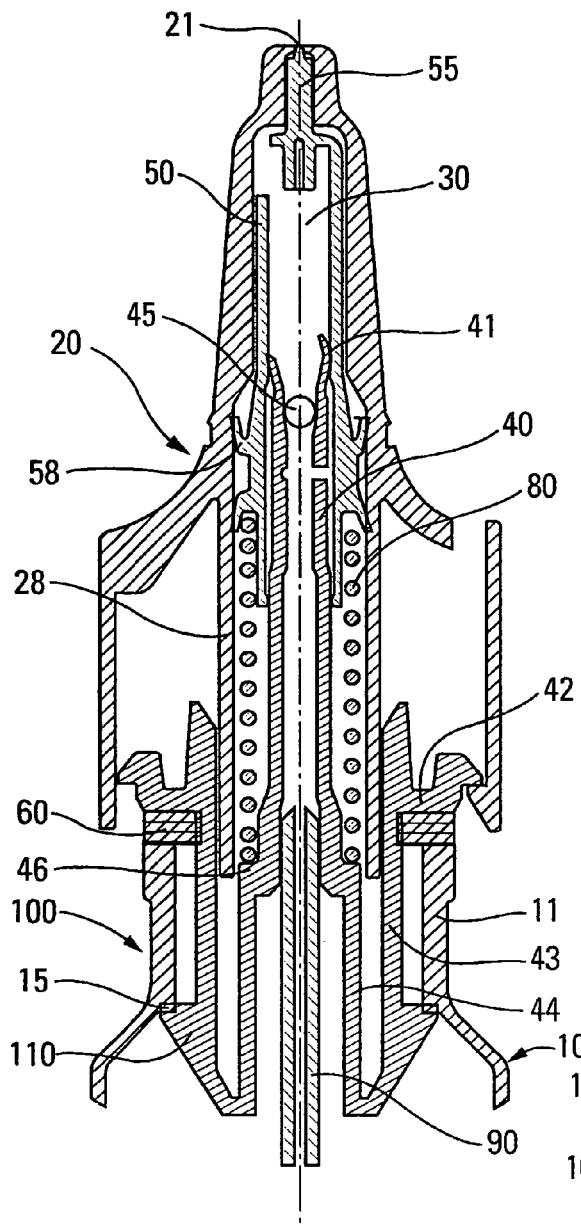
FIG. 7 is a view similar to the view in FIG. 5, showing another variant embodiment of the fastener means in the assembled position.

The invention relates to a fluid dispenser device including a reservoir 10 containing a fluid, e.g. a pharmaceutical, a cosmetic, or a perfume. The reservoir 10 preferably includes a neck 11 defining an opening making it possible to insert and to fasten a dispenser member, such as a pump, as described below. A dispenser head 20 is assembled in movable manner relative to the reservoir 10, the head 20 including a dispenser orifice 21 through which the fluid is dispensed at each actuation. A metering chamber 30 is also defined in which a piston 40 slides between a rest position and a dispensing position. The metering chamber makes it possible to define accurately the quantity of fluid that is dispensed at each actuation, the displacement of said piston 40 causing a measured dose of fluid to be expelled.

In the invention, said piston 40 is mounted in stationary manner on said reservoir 10 by being made integrally either directly with the reservoir, or with fastener means that are adapted to be fastened on said reservoir. It is thus possible to save on at least one component part compared to existing assemblies. The various figures show several embodiments of the invention. Thus, in FIG. 21, said piston 40 is made integrally with said reservoir 10, and in this embodiment the fluid can be inserted into the reservoir via the bottom of said reservoir, with an appropriate plug then being fitted in any appropriate way, so as to close the reservoir in leaktight manner. In the other figures, the piston 40 is fastened on the reservoir by fastener means 100. The various fastener means are described below with reference to the various figures that show various embodiments.

The various figures show a particular fluid dispenser device, but naturally the present invention is not limited to the characteristics shown, in particular with regard to the portions of the device that do not form the fastener means 100 for fastening the piston 40 on the reservoir 10. Thus, the dispenser head 20 can be of any shape, and the orifice 21 is not necessarily axial. In addition, in the embodiments shown, the piston 40 slides in a cylinder 50 forming a pump body inside which the metering chamber 30 is defined. The pump body 50 is advantageously made integrally with a closure member 55 that is disposed upstream from the dispenser orifice 21. In addition, the pump body 50 includes a second piston 58 that is adapted to slide in a cylinder 28 of the dispenser head 20. A return spring 80 urges said closure member 55 towards its closed position for closing the dispenser orifice 21, and, during actuation, said closure member can slide towards an open position for opening the dispenser orifice 21, under the effect of the pressure of the fluid that displaces said second piston 58 in the cylinder 28 against the force of the return spring, so as to open the dispenser orifice and make it possible to expel the dose of fluid contained in the metering chamber 30. While the closure member 55 is being displaced, the piston 40 slides in the body 50 so as to dispense the dose. An inlet valve 45 is advantageously provided upstream from the metering chamber 30, and the inlet valve can advantageously be formed on said piston 40. In the embodiment shown, the valve seat is formed on the piston 40, and the valve element is a ball 45. Naturally, any other form of inlet valve can be envisaged. A dip tube 90 can be assembled in the piston 40 so as to make it possible to expel all the fluid contained in the reservoir 10. The cylinder 28 of the dispenser head 20 advantageously extends inside the neck 11 of the reservoir 10 when the device is in its actuated or dispensing position, so as to improve the stability of the assembly and reduce the overall size of the device. In order to provide stability and a simple and easy way of fastening the piston 40 on the reservoir 10, the piston 40 advantageously includes, at its end remote from the sealing portion 41 that forms the piston proper and that slides in the pump body 50, a radial flange 42 for resting on the top edge of the neck 11 of the reservoir 10, said flange 42 being extended by an axial well 43 that penetrates inside the neck 11 of the reservoir 10, and that is connected to a tubular portion 44 that is also axial, and that includes, at its top end, (in the orientation shown in the figures) said piston-forming sealing portion 41. The tubular element 44 advantageously includes a shoulder 46 that is adapted to receive the end of the return spring 80 that is remote from the second piston 58 of the pump body 50. The tubular element 44 is hollow and connects the dip tube 90 to the inlet valve 45 and therefore to the metering chamber 30. Advantageously, the dispenser head 20 is also snap-fastened on the piston 40 or on the neck 11 of the reservoir 10, or on any element that is secured to either of these two elements, so as to avoid any risk of said head 20 being removed from said reservoir 10 in unwanted or accidental manner. As explained above, these various characteristics are shown only by way of example, and other variants (not shown) could also be envisaged.

Figure 21:
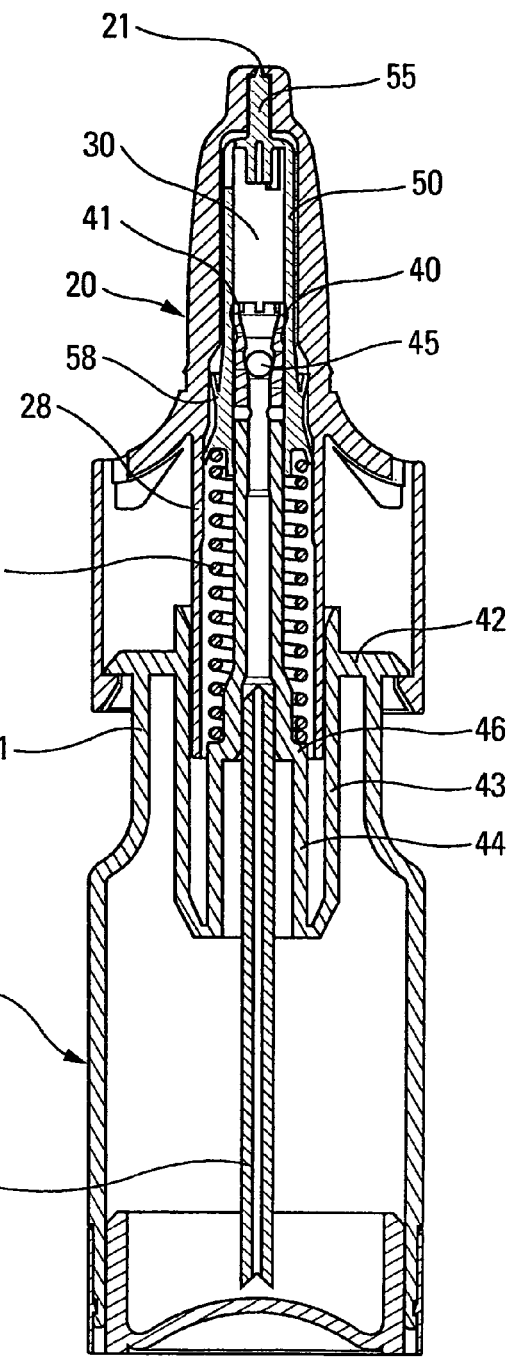
FIG. 21 is a view similar to the view in FIG. 20, also showing still another embodiment of the present invention.

In a first embodiment of the invention, shown in FIG. 21, the piston 40 is therefore made integrally with the reservoir 10.

In another embodiment of the invention, the piston 40 is fastened to the outside of the neck 11 of the reservoir. FIGS. 1 to 4 show such a fastening by snap-fastening. To this end, snap-fastener means forming a snap-fastener profile 120 co-operating with the outside of the neck 11 are provided, preferably made integrally with the piston 40. The neck 11 can advantageously include a complementary snap-fastener profile 16 for co-operating with the snap-fastener profile 120 of the snap-fastening means. A gasket 60 is preferably interposed between the piston 40 and the neck 11 of the reservoir. As shown in FIGS. 1 to 4, the gasket is preferably deformed while the piston 40 is being fastened on the reservoir 10, thereby providing good sealing at this location.

FIGS. 3a and 3b show a variant embodiment of the gasket 60 that includes a sealing profile 61 that is adapted to co-operate with a complementary sealing profile 70 provided on the outer surface of the axial well 43 of the piston 40 that extends inside the neck 11 of the reservoir. In the embodiment shown, the complementary snap-fastener profile 70 is made in the form of a projection that co-operates, for example, with two flexible tabs 61 of the gasket 60 that are flattened against said projection while the piston 40 is being fastened on the reservoir 10.

FIG. 4 shows a variant embodiment in which the snap-fastener profile 70 is formed on the inside surface of the neck 11 of the reservoir, in which embodiment the gasket 60 also advantageously includes a complementary snap-fastener profile 61, but which is disposed on the opposite side compared to the variant shown with reference to FIGS. 3a and 3b. Naturally, in a variant to snap-fastening, it is also possible to envisage fastening by means of a thread or crimping to the outside of the neck 11 of the reservoir.

In another variant embodiment of the invention, the piston is fastened to the inside of the neck 11 of the reservoir 10. FIG. 5 shows an embodiment in which the axial well 43 of the piston 40 is force fitted directly inside the neck 11 of the reservoir. Both fastening and sealing are obtained by this force fit, which can be particularly secure since the force-fitted portion no longer forms the pump body in which the piston of the pump must slide. The force-fitted portion can therefore deform as much as necessary while being force fitted, so as to be positioned securely inside the neck of the reservoir.

FIG. 6 shows a variant embodiment in which a screw thread 80 is provided on the piston 40, in particular on the axial well 43, and which co-operates with a corresponding thread 85 provided inside the neck 11 of the reservoir. Advantageously, a gasket 60 is interposed between the piston 40 and the top edge of the reservoir 10, and means can be provided for preventing unscrewing, e.g. made in the form of a broken portion on one or the other of said threads 80, 85.

Figure 8:
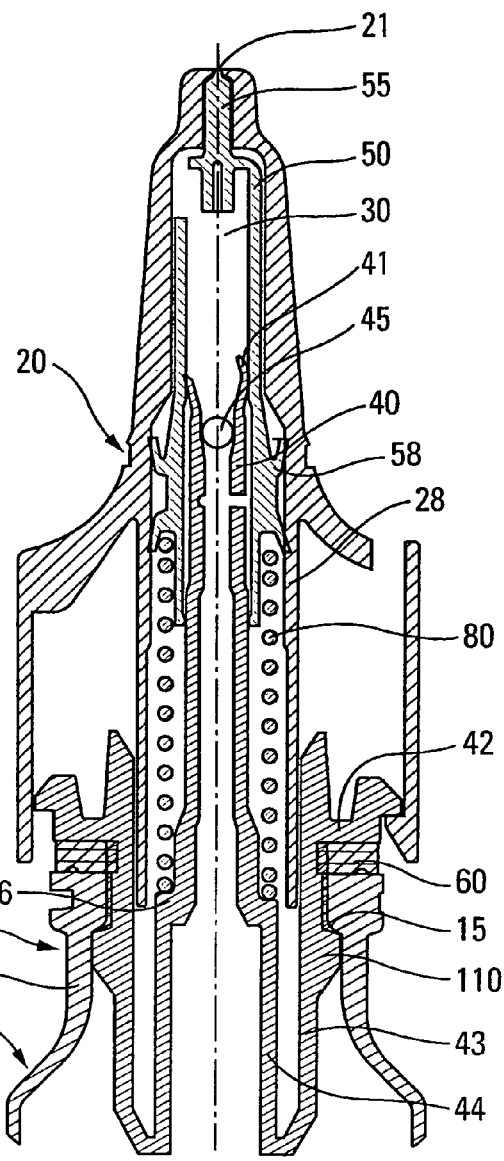
FIG. 8 is a view similar to the views in FIGS. 5 and 7, showing still another variant embodiment of the present invention.
Figure 9:
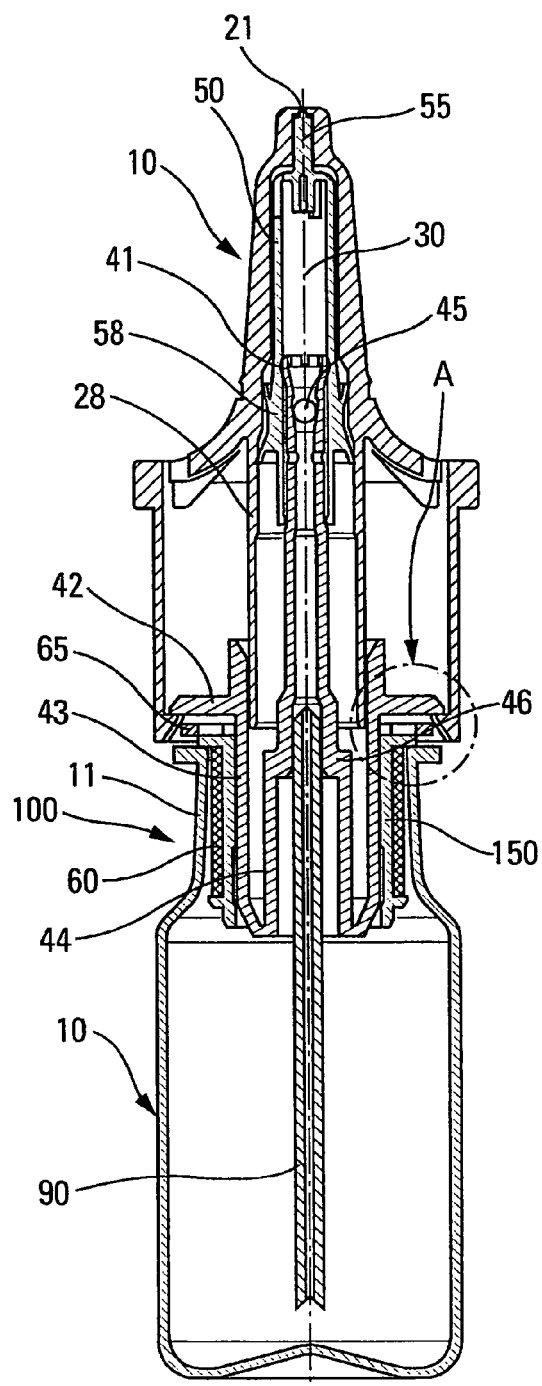
FIGS. 9 to 10 show diagrammatic section views of a fluid dispenser device constituting still another variant embodiment of the invention, respectively before and after assembly.
Figure 10:
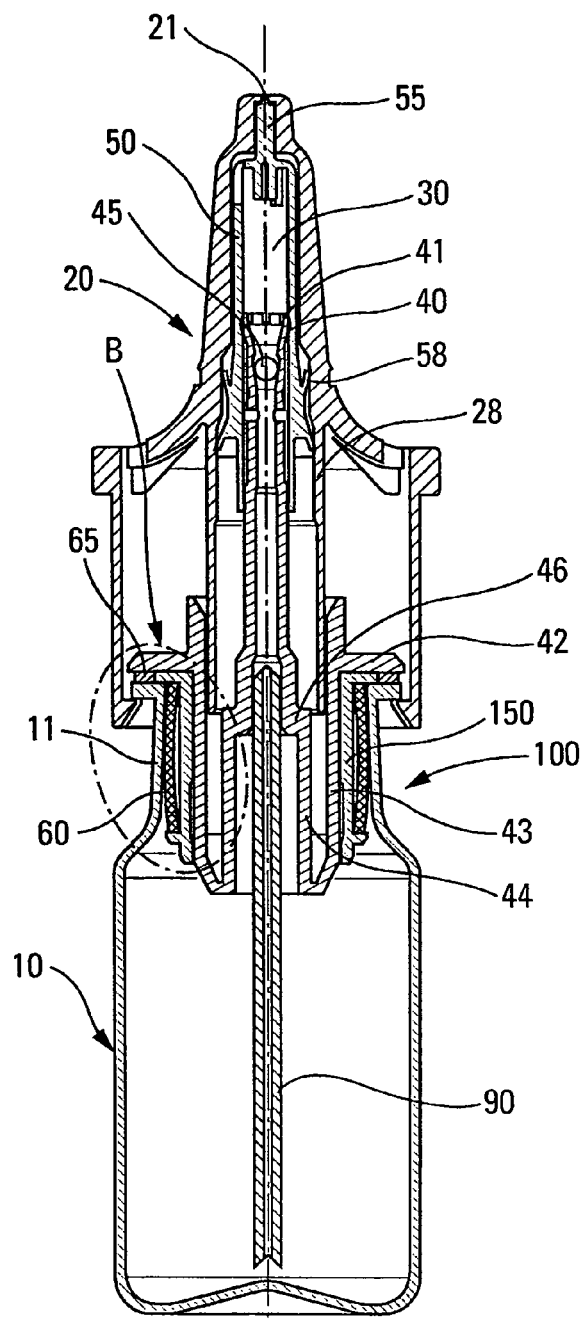

FIGS. 7 and 8 show two variant embodiments of snap-fastening inside the neck 11 of the reservoir 10. In both cases, the piston 40, in particular the axial well 43, includes snap-fastener means comprising a snap-fastener profile 110 that is adapted to co-operate with the neck 11 of the reservoir. A complementary snap-fastener profile 15 can advantageously be provided inside said neck 11. Once again, such snap-fastening is made possible because the piston 40, at its portion that is fastened on the neck 11 of the reservoir 10, does not define a slide surface that might be deformed in irreversible manner during fastening, which would risk spoiling proper operation of the device. On the contrary, the structure that is shown and described above of the piston 40 enables said piston to deform inwards, and therefore enables it to be snap-fastened easily inside the neck 11 of the reservoir. Once again, a gasket 60 can be interposed between the piston 40 and the reservoir 10.

FIGS. 9 to 13b show other variant embodiments. In these embodiments, a gasket 60 is interposed between the piston 40 and the inside surface of the neck 11 of the reservoir. FIGS. 9, 10, 11a, and 11b show a first variant embodiment. In this first variant, a bushing 150 is also interposed between the piston 40 and the neck 11 of the reservoir, the bushing 150 receiving the gasket 60. The gasket 60 can include an end extension 65 that is deformed at the last moment while the device is being assembled, this deformation compressing the gasket 60, thereby ensuring good sealing. As can be seen in FIGS. 9, 10, 11a, and 11b, the bushing 150 includes a top shoulder and a bottom shoulder between which there is disposed the gasket 60 in a non-stressed state before assembly. During the final assembly stage, the top extension 65 of the gasket 60 is deformed, in this example by being displaced axially downwards, thereby causing the gasket 60 to expand over the inside surface of the neck 11 of the reservoir. This radial expansion both seals and fastens the piston 40 in the reservoir 10.

Figure 12A:
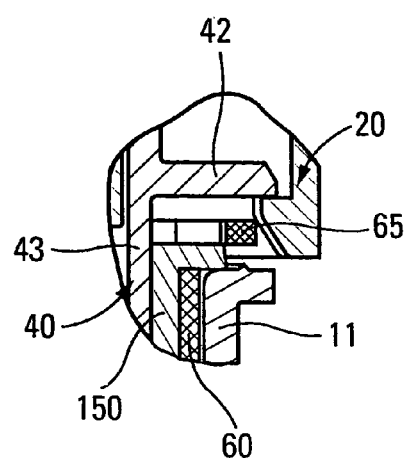
FIGS. 12a and 12b are views similar to the views in FIGS. 11a and 11b, showing a variant embodiment of the present invention.
Figure 12B:
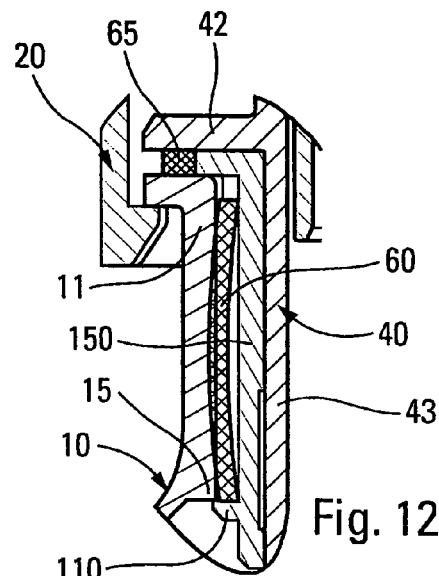
Figure 11A:
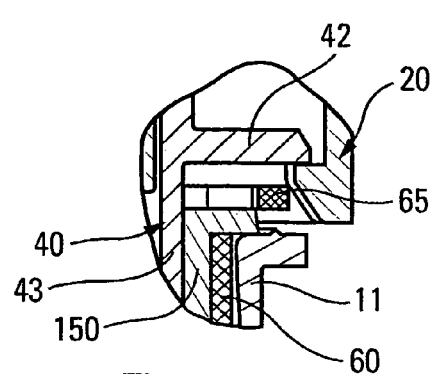
FIGS. 11a and 11b are large-scale diagrammatic section views of details A and B in FIGS. 9 and 10.
Figure 11B:
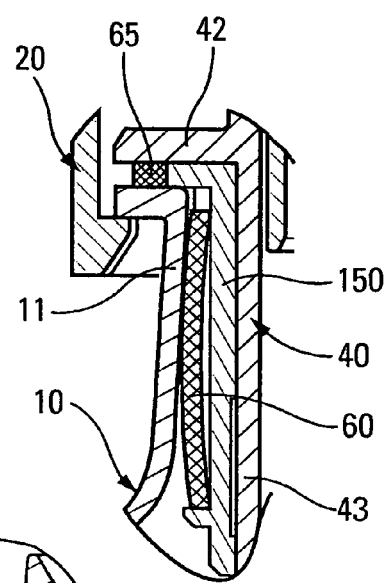

FIGS. 12a and 12b show a variant of the embodiment described above, in which the bottom shoulder of the bushing 150 further includes a snap-fastener profile 110 that becomes snap-fastened to, or caught by barbs against, the complementary profile 15 provided inside the neck 11 of the reservoir.

Figure 13A:
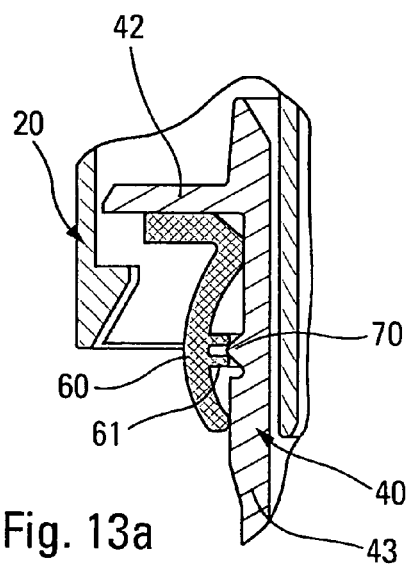
FIGS. 13a and 13b are views similar to the views in FIGS. 12a and 12b, showing another variant embodiment of the invention.
Figure 13B:
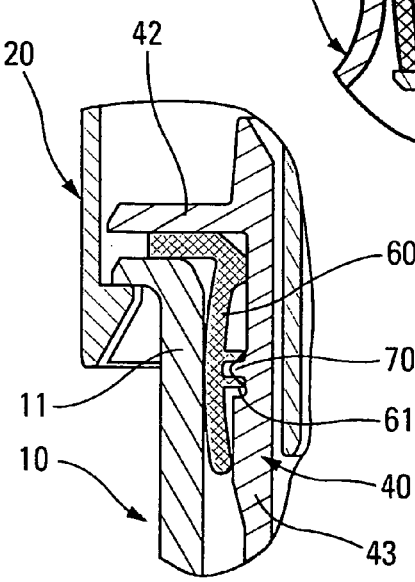

FIGS. 13a and 13b show another variant embodiment, in which there is no bushing, but in which the gasket 60 is similar to the gasket described with reference to FIGS. 3a and 3b. This variant differs from the variant in FIGS. 3a and 3b by the absence of snap-fastener means on the outside of the neck 11 of the reservoir. In this embodiment, fastening is therefore also provided by radially clamping the gasket 60 between the neck 11 of the reservoir 10 and the axial well 43 of the piston 40.

FIGS. 14 to 19 show still another variant embodiment. In this variant embodiment, the gasket 60 includes a projection 65 that is adapted to deform while the piston 40 is being assembled, such that it comes to be positioned below the neck 11 of the reservoir, inside said reservoir, so as to fasten the device in permanent manner and provide improved sealing. FIGS. 16 and 17, that are large-scale views of details C and D in FIGS. 14 and 15, clearly show how the projection 65, which before assembly bears against the piston 40, is deformed during assembly by the frustoconical shape of the bottom end of the axial well 43 of the piston that co-operates with said projection 65. FIGS. 18 and 19 show two variant embodiments, respectively before and after assembly, FIG. 18 showing a bushing 150 interposed between the piston 40 and the neck 11 of the reservoir, the gasket 60 being interposed between the bushing 150 and the neck 11. FIG. 19 shows a gasket 60 co-operating with a gasket portion in the form of a radial flange that is made of a different material, thereby making is possible to adapt the sealing and flexibility requirements. All of the gaskets described with reference to FIGS. 9 to 19 are advantageously made by overmolding, in particular when they are for co-operating with a bushing 150, as shown in FIGS, 11a to 12b. In this event, the gasket 60 is injected around said bushing 150, thereby making it possible to form said top extension 65 that comes to deform the gasket 60 at the end of assembly.

Figure 20:
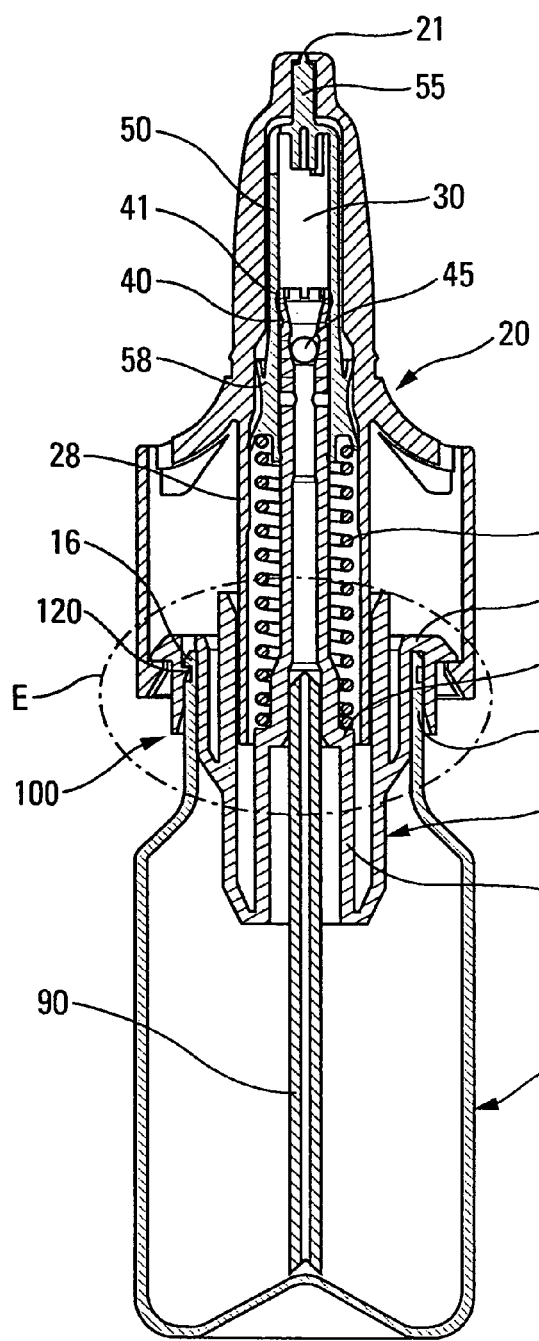
FIG. 20 is a diagrammatic section view of a fluid dispenser device constituting still another embodiment of the present invention.

FIGS. 20 and 22 to 24 show another embodiment in which the piston is fastened both to the inside and to the outside of the neck 11 of the reservoir 10. With reference to FIGS. 20 and 22, FIG. 22 being a larger-scale view of a detail E in FIG. 20, it should be observed that the piston 40 includes an outer snap-fastener profile 120 co-operating with a corresponding profile 16 provided on the outside of the neck 11 of the reservoir, said reservoir neck further including flanges or other internal profiles on its inside surface that are adapted to co-operate with the piston 40 so as to provide sealing. Naturally, the profiles could also be provided on the piston 40 rather than in the neck 11 of the reservoir. In this embodiment, fastening is therefore achieved by snap-fastening to the outside of the neck of the reservoir, and by being force fitted inside the neck.

FIG. 23 shows a variant embodiment in which the piston 40 is fastened to the neck 11 of the reservoir by snap-fastening both to the inside and to the outside thereof. In this embodiment, the piston 40 includes inner and outer snap-fastener profiles 110, 120 that co-operate with respective corresponding snap-fastener profiles 15 and 16 of the neck of the reservoir 11.

Finally, in the embodiment in FIG. 24, the top edge of the neck 11 of the reservoir 10 includes two axial branches 18 and 19 that are substantially parallel, each co-operating with the piston 40, preferably with a gasket 60 interposed therebetween. In this embodiment, snap-fastening can be performed inside one of the branches 18, while the other branch can support said gasket 60. Naturally, different fastener and sealing means could be envisaged with such a complex configuration of the neck of the reservoir. It should be observed that the dual inner and outer snap-fastening could also be used to fasten a pump body to a reservoir.

The present invention therefore makes it possible to make a fluid dispenser device that is simple and easy to assemble, with assembly not presenting any risk to the operation of the pump, and in particular not spoiling in any way the slide surface of the pump body 50 or of the piston 40 itself at its sealing portion 41 that is slidable in said pump body 50. On the contrary, as a result of fastening the piston 40 directly on the reservoir, in contrast to a conventional device in which it is the pump body that is fastened to the reservoir, it is possible to achieve such fastening in a wide variety of different ways that are safe, simple, and reliable. Another advantage of this embodiment is that it makes it possible to form the metering or pump chamber 30 directly upstream from the dispenser orifice 21, thereby making it possible to make the closure member 55 and the outlet valve of the metering chamber 30 as a single part. It is therefore no longer necessary to provide an outlet valve for the metering chamber, and then, after an expulsion channel extending through the dispenser head, a separate closure member in the dispenser orifice, as is the situation in most existing devices. The present invention therefore makes it possible to make a pump that is more compact, comprising fewer parts, and that is therefore less costly. In addition, the present invention includes only one spring 80 that acts as a return spring for returning the pump and for closing the closure member 55, whereas, in existing devices, when a closure member exists that is placed directly upstream from the dispenser orifice 21, there are generally two springs, one for urging the closure member towards its closed position, and the other for returning the piston towards its rest position. The present invention therefore makes it possible in this respect also to improve and to simplify prior-art pumps.

Naturally, the invention is described above with reference to several variant embodiments and with reference to the drawings, but said variant embodiments are not limiting, and, on the contrary, various modifications could be applied thereto by the person skilled in the art, without going beyond the ambit of the present invention, as defined by the accompanying claims.

The invention claimed is:

1. A fluid dispenser device comprising: a reservoir (10); a dispenser head (20) including a dispenser orifice (21) disposed at a terminal end of the dispenser head (20), wherein fluid is dispensed out of the fluid dispenser device via the dispenser orifice; a metering chamber (30) disposed directly upstream from the dispenser orifice (21); and a piston (40) that is slidable in said metering chamber (30) between a rest position and a dispensing position, said piston (40) being mounted in stationary manner on said reservoir (10), said piston is made integrally with said reservoir (10) and/or with fastener means (100) that are adapted to be fastened on said reservoir (10); and wherein said piston (40) slides in a pump body (50) disposed in the dispenser head (20);

said pump body (50) forms part of a closure member (55) that cooperates directly with the dispenser orifice and is slidable in said dispenser head (20) between a closed position and an open position of the dispenser orifice (21).

2. A device according to claim 1, in which said piston (40) is fastened on the reservoir (10) by fastener means (100), said fastener means (100) being connected integrally with said piston (40).

3. A device according to claim 2, in which said fastener means (100) are snap-fastener, force-fit, or screw-fastener means.

4. A device according to claim 2, in which said piston (40) is fastened to the outside of a neck (11) of said reservoir (10).

5. A device according to claim 2, in which said piston (40) is fastened to the inside of a neck (11) of said reservoir (10).

6. A device according to claim 2, in which said piston (40) is fastened both to the outside and to the inside of a neck (11) of said reservoir (10).

7. A device according to claim 1, in which said piston (40) is made integrally with said reservoir (10).

8. A device according to claim 1, in which said closure member (55) includes a second piston (58) that is slidable in a cylinder (28) of said dispenser head (20).

9. A device according to claim 1, in which said piston (40) includes an inlet valve (45) of the pump chamber (30).

10. A device according to claim 1, in which said piston (40) is fastened on the reservoir (10) with a gasket (60) interposed between the piston (40) and the reservoir (10).

11. A device according to claim 10, in which said gasket (60) is deformed while said piston (40) is being fastened on said reservoir (10).

12. A device according to claim 10, in which the piston (40) includes fastener means (100) co-operating with the outside of a neck (11) of the reservoir (10), said gasket (60) co-operating with the inside of said neck (11).

13. A device according to claim 10, in which the piston (40) includes fastener means (100) co-operating with the inside of a neck (11) of the reservoir (10).

14. A device according to claim 13, in which said fastener means (100) include said gasket (60) that is deformed between the piston (40) and the inside of the neck (11) of the reservoir (10), so as to fasten the piston (40) in said neck (11) by a leaktight force fit.

15. A device according to claim 12, in which one amongst the inside surface of the neck (11) of the reservoir (10) and the corresponding outside surface of the piston (40) includes a sealing profile (70) co-operating with said gasket (60) in the mounted state, preferably with a complementary sealing profile (61) of said gasket (60).

16. A device according to claim 13, in which said gasket (60) includes a projection (65) that, while the piston (40) is being fitted by force, is itself deformed below the neck (11) of the reservoir (10), inside said reservoir, so as to fasten the piston (40) in permanent manner.

17. A device according to claim 1, in which said piston (40) includes snap-fastener means (110, 120) co-operating with the inside surface and/or the outside surface of a neck (11) of said reservoir (10).

18. A device according to claim 17, in which said snap-fastener means (110, 120) comprise a snap-fastener profile (110, 120) that is adapted to be snap-fastened in said neck (11) or around said neck.

19. A device according to claim 18, in which said neck (11) includes a complementary snap-fastener profile (15, 16) co-operating with said snap-fastener profile (110, 120) of said piston (40).

20. A device according to claim 1, in which the piston (40) includes a screw thread (80) co-operating with a corresponding thread (85) provided on the inside or on the outside a neck (11) of said reservoir (10).

21. A device according to claim 20, in which at least one of said threads (80, 85) includes means for preventing unscrewing, such as a broken portion.

22. A device according to claim 1, in which said piston (40) includes first snap-fastener means (110) co-operating with the inside of a neck (11) of the reservoir (10), and second snap-fastener means (120) co-operating with the outside of said neck (11).

23. A device according to claim 22, in which the inside and/or the outside of said neck (11) includes a complementary snap-fastener profile (15, 16).

24. A device according to claim 1, in which the top edge of a neck (11) of the reservoir (10) includes two axial branches (18, 19) each co-operating with said piston (40), preferably with a gasket (60) being interposed therebetween.

25. A device according to claim 18, in which said fastener means (110, 120) are formed directly on the piston.

26. A device according to claim 1, in which a bushing (150) is interposed between the piston (40) and a neck (11) of said reservoir (10).

27. A device according to claim 26, in which said snap-fastener means (110) are formed on said bushing (150).

28. A device according to claim 26, in which a gasket (60) is interposed between said bushing (150) and the neck (11) of the reservoir (10).

29. A device according to claim 1, in which said piston (40) is force fitted directly inside a neck (11) of said reservoir (10).

30. A fluid dispenser device comprising:
a reservoir;
a dispenser head comprising a dispenser orifice at a distal end of the dispenser head, wherein fluid is dispensed out of the fluid dispenser device via the dispenser orifice;
a pump body comprising a metering chamber; and
a piston slidable in the metering chamber between a rest position and a dispensing position, the piston fixed relative to the reservoir and integral with at least one of the reservoir or a fastener on the reservoir;
the pump body comprising a closure member that cooperates with the dispenser orifice and is slidable in the dispenser head between a closed position in which the closure member closes the dispenser orifice and an open position in which the closure member is retracted from the dispenser orifice.

31. The device according to claim 30, wherein the closure member is an integral one-piece construction with the pump body.

* * * * *